US00PP18752P2

(12) United States Plant Patent
Bradford

(10) Patent No.: US PP18,752 P2
(45) Date of Patent: Apr. 22, 2008

(54) NECTARINE TREE NAMED 'JUNE SWEET'

(50) Latin Name: *Prunus persica*
Varietal Denomination: June Sweet

(76) Inventor: Lowell Glen Bradford, 10237 E. Mariposa Way, Le Grand, CA (US) 95333

( * ) Notice: Subject to any disclaimer, the term of this patent is extended or adjusted under 35 U.S.C. 154(b) by 0 days.

(21) Appl. No.: 11/637,898

(22) Filed: Dec. 13, 2006

(51) Int. Cl.
*A01H 5/00* (2006.01)

(52) U.S. Cl. ..... Plt./190
(58) Field of Classification Search ..... Plt./190
See application file for complete search history.

(56) References Cited

U.S. PATENT DOCUMENTS

PP10,884 P * 5/1999 Bradford

* cited by examiner

*Primary Examiner*—Kent Bell

(57) ABSTRACT

The present invention relates to a nectarine tree, *Prunus persica,* and more particularly to a new and distinct variety broadly characterized by a large size, vigorous, hardy, self-fertile, productive and regular bearing tree. The fruit matures under the ecological conditions described in mid June, with first picking on Jun. 21, 2006. The fruit is uniformly large in size, sub-acidic and sweet in flavor, globose to somewhat oblong in shape, clingstone in type, firm in texture, yellow in flesh color, and full red in skin color.

1 Drawing Sheet

Botanical classification: *Prunus persica.*
Variety denomination: 'June Sweet'.

BACKGROUND OF THE VARIETY

In a continuing effort to improve the quality of shipping fruits, I, the inventor, typically hybridize a large number of peach, nectarine, plum, apricot, and cherry seedlings each year. I also grow a lesser number of open pollinated seeds of each of these fruits, usually to capture recessive traits. The present invention relates to a new and distinct variety of nectarine tree, which has been denominated varietally as 'June Sweet'.

During the spring of 2000 I gathered fruit from a 'Kay Sweet' (U.S. Plant Pat. No. 10,884) nectarine tree in my experimental orchard located near Le Grand, Calif., in Merced County (San Joaquin Valley). I used embryo rescue techniques to germinate the seeds from this fruit, grew them as seedlings on their own root in my greenhouse, and upon reaching dormancy transplanted them to a cultivated area in the experimental orchard described above. During the fruit evaluation season of 2003 I selected the claimed variety as a single tree from the group of seedlings described above. Subsequent to origination of the present variety of nectarine tree, I asexually reproduced it by budding and grafting in the experimental orchard described above, and such reproduction of plant and fruit characteristics were true to the original plant in all respects. The reproduction of the variety included the use of 'Nemaguard' rootstock (unpatented) upon which the present variety was compatible and true to type.

The present variety is most similar to its parent, 'Kay Sweet' (U.S. Plant Pat. No. 10,884) nectarine, by producing nectarines that are very firm in texture, clingstone in type, sub-acidic in flavor, yellow in flesh color, and full red in skin color, but is distinguished therefrom by producing fruit that is larger in size, that is sweeter in flavor, and that matures about eighteen days later.

SUMMARY OF VARIETY

In summary, the present variety is characterized by a large size, vigorous, hardy, self-fertile, productive and regular bearing tree. The fruit matures under the ecological conditions described in mid June, with first picking on Jun. 21, 2006. The fruit is uniformly large in size, sub-acidic and sweet in flavor, globose to slightly oblong in shape, clingstone in type, firm in texture, yellow in flesh color, and full red in skin color.

DRAWING

The accompanying photograph consists of four whole fruits positioned to display the characteristics of the skin color and form, one fruit divided transversely to the suture plane to reveal the flesh and stone, various leaves, two insets showing buds and blossoms in various stages, and a typical tip shoot.

POMOLOGICAL CHARACTERISTICS

Referring now more specifically to the pomological characteristics of this new and distinct variety of nectarine tree, the following has been observed under the ecological conditions prevailing near Le Grand, Merced County (San Joaquin Valley), Calif., and was developed at the state of shipping ripe on Jun. 24, 2006, on the original tree during its sixth growing season. All major color code designations are by reference to the Inter-Society Color Council, National Bureau of Standards. Common color names are also used occasionally.

Tree

Size: Large, reaching and maintaining a height of 12' [3.66 m.] and a spread of 9' [2.74 m.] after six growing seasons utilizing typical dormant pruning.

Vigor: Vigorous, responding typically to irrigation and fertilization. The variety grows about 3' [0.91 m.] of surplus top-growth during the spring and summer. The plant should be grown on a standard commercial rootstock for production purposes.

Growth: Upright and dense.

Form: Pruned to a central leader form.

Hardiness: Hardy with respect to central California winters.

Heat tolerance: Observed to perform adequately in typical central California climatic conditions, which typically include extended periods of heat.

Drought tolerance: Variety is developed for commercial orchards and requires regular irrigation.

Production: Productive, thinning necessary.

Fertility: Self-fertile.

Bearing: Regular bearer with no alternate bearing yet observed.

Approximate chilling requirement: 500 hours.

Trunk:

*Size.*—Medium, reaching a maximum diameter of 4½" [114 mm.] after the sixth growing season.

*Texture.*—Shaggy.

*Bark color.*—A Brownish gray [64. brGy] and Dark brown [59. d.Br] variegation.

*Lenticels.*—Approximate Number Per Square Inch: 6. Color: Moderate orange yellow [71. m.OY]. Typical Size: ¼" [6.4 mm.] to ½" [12.7 mm.]. Shape: Eye-shaped to elongated.

Branches:

*Size.*—Diameter of first lateral is 1¼" [32 mm.] measured 12" from the central leader.

*Texture.*—Smooth on first and second year wood, increasing roughness with age.

*Color.*—1st Year Wood Topside: Grayish red [19. gy.R]. 1st Year Wood Underside: Brilliant yellow green [116. brill.YG]. Older Wood: Deep yellowish brown [75. deep yBr].

*Lenticels.*—Number Per Square Inch: More than 80 on second year wood. Color: Light yellowish brown [76. l.yBr]. Typical size: 1/64" [0.4 mm.] to 3/32" [2.4 mm.] on second year wood. Shape: Elongated.

Leaves:

*Size.*—Large. Average Length: 6⅝" [168 mm.]. Average width: 1¾" [44 mm.].

*Arrangement.*—Alternate.

*Thickness.*—Medium.

*Form.*—Elliptical.

*Apex.*—Acuminate.

*Base.*—Acute, with an average base angle of 75 to 85 degrees.

*Surface.*—Smooth.

*Color.*—Dorsal Surface: Deep yellow green [118. deep YG]. Ventral Surface: Moderate yellow green [120. m.YG].

*Margin.*—Finely serrate.

*Venation.*—Pinnately net veined.

*Petiole.*—Average Length: ½" [12.7 mm.]. Average Thickness: 1/16" [1.6 mm.]. Color: Strong yellow green [117. s.YG].

*Stipules.*—Number: 2 per leaf, up to 6 per growing tip. Average Length: ¼" [6.4 mm.]. Color: Strong yellow green [117. s.YG] turning Strong reddish brown [40. s.rBr] with maturity.

*Glands.*—Number: 2 to 4 per leaf. Position: Both alternately and oppositely positioned on both the petiole and base of blade. Size: Medium. Form: Reniform. Color: Strong yellow green [117. s.YG] on younger leaves turning Moderate reddish brown [43. m.rBr] in the center with maturity.

*Leaf buds.*—Medium in size, pointed.

Flower buds:

*Hardiness.*—Hardy, with respect to central California winters.

*Diameter.*—Typically ⅜" [9.5 mm.] 1 week before bloom.

*Length.*—Typically 7/16" [11.1 mm.] 1 week before bloom.

*Form.*—Not appressed.

*Surface.*—Pubescent.

*Color.*—Moderate purplish pink [250. m.pPk].

Flowers: Perfect, complete, perigynous, usually a single pistil, typically thirty or more stamens, five sepal and petal locations alternately positioned.

*Type.*—Showy, large.

*Average flower diameter.*—1 15/16" [49.2 mm.].

*Number of petals.*—Usually five, with some double blossoms and extra petals fragments observed.

*Petal shape.*—Circular to oval.

*Petal margin.*—Somewhat wavy.

*Average petal diameter.*—13/16" [20.6 mm.].

*Average petal length.*—13/16" [20.6 mm.].

*Petal apex.*—Rounded.

*Petal base.*—Rounded to somewhat truncate.

*Petal color.*—Pale pink [7. p.Pk] toward the apex, Moderate purplish pink [250. m.pPk] toward the base.

*Anther color.*—Dark red [16. d.R] over a Light yellow [86. l.Y] center at bloom onset.

*Stigma color.*—Light greenish yellow [101. l.gY].

*Sepal color.*—Dark purplish red [259. d.pR].

*Sepal length.*—¼" [6 mm.].

*Sepal width.*—3/16" [5 mm.].

*Average pistil length.*—¾" [19.1 mm.].

*Average stamen length.*—⅝" [15.9 mm.].

*Fragrance.*—Moderate.

*Blooming period.*—Somewhat early compared with other varieties.

*Onset of bloom.*—One percent on Feb. 17, 2006.

*Date of full bloom.*—Mar. 1, 2006.

*Duration of bloom.*—One to two weeks, dependent on ambient temperature.

*Number per cluster.*—1 to 3 with single flowers most common.

FRUIT

Maturity when described: Firm ripe, Jun. 24, 2006.

Date of first picking: Jun. 21, 2006.

Date of last picking: Jul. 4, 2006.

Size: Uniform, large.

*Average diameter axially.*—3⅛" [79.4 mm.].

*Average diameter across cheek plane.*—2 15/16" [74.6 mm.].

*Average diameter across suture plane.*—2 15/16" [74.6 mm.].

*Typical weight.*—7.5 ounces [213 grams].

Form: Uniform, symmetrical, globose to oblong.

*Longitudinal section form.*—Oval to somewhat obovate.

*Axial view form.*—Round.

Suture: A shallow groove extending from the stem to about ⅝" [15.9 mm.] beyond the pistil point, sharper toward the apex and in the stem cavity.

Ventral surface: Rounded, lipped throughout.
Lips: Slightly unequal.
Cavity: Flaring, elongated in the suture plane, suture showing on both sides, Strong yellow [84. s.Y] stem markings typical.
*Depth.*—⅝ [15.9 mm.].
*Breadth.*—1½" [38.1 mm.].
Base: Round to truncate, slightly cordate if viewed parallel to the suture.
Apex: Rounded.
Pistil point: Apical, a very short 1/32" [0.8 mm.] average length, often depressed within the suture.
Stem: Medium.
*Average length.*—⅜" [9.5 mm.].
*Average width.*—3/16" [4.8 mm.].
Skin:
*Thickness.*—Medium.
*Surface.*—Smooth.
*Tenacity.*—Tenacious to flesh.
*Astringency.*—Non-astringent.
*Tendency to crack.*—None observed.
*Color.*—Very dark red [17. v.d.R] smoothly blending into a Deep red [13. deep R] background color with slight Moderate yellow [87. m.Y] freckling toward the apex.
Flesh:
*Color.*—Light Yellow [86. l.Y] from the stone to skin at this maturity, but will acquire a very slight amount of Strong red [12. s.R] flecking near the stone with maturity.
*Surface of pit cavity.*—Light yellow [86. l.Y] fibers breaking when twisted from the stone.
*Amygdalin.*—Scarce.
*Juice.*—Abundant, rich.
*Texture.*—Firm, crisp, melting.
*Fibers.*—Abundant, fine.
*Ripens.*—Slightly earlier toward the apex.
*Flavor.*—Sub-acid and sweet, typically 18 brix.
*Aroma.*—Moderate to slight.
*Eating quality.*—Excellent.

STONE

Type: Clingstone.
Form: Oval.
Hilum: Narrow, oblong.
Base: Straight, rounded.
Apex: Acuminate, with an average tip length of ⅛" [3.2 mm.] and an average angle of 40 to 50 degrees.
Sides: Slightly unequal.
Surface: Irregularly furrowed and ridged near the apex, pitted from base to above center.
Ridges: Rounded.
External color of stone: Dark orange yellow [72. d.OY] when freshly removed.
Pit wall color when cracked: Light yellowish brown [76. l.yBr] when freshly cracked.
Cavity surface color: Light yellowish brown [76. l.yBr].
Average pit wall thickness: ¼" [6.4 mm.].
Average width: 1⅛" [28.6 mm.].
Average length: 1⅝" [41.3 mm.].
Average breadth: ⅝" [15.9 mm.].
Tendency to split: Slight.
Kernel:
*Form.*—Oval.
*Skin color.*—Light yellow [86. l.Y] when freshly removed.
*Pellicle color.*—Light olive brown [94. l.OlBr].
*Vein color.*—Strong yellow [84. s.Y].
*Taste.*—Bitter.
*Viable.*—Yes.
*Average width.*—½" [12.7 mm.].
*Average length.*—13/16" [20.6 mm.].
*Amygdalin.*—Moderate.

USE

Market: Fresh market and long distance shipping.
Keeping quality: Good, fruit quality observed to remain in good condition after 21 days in standard cold room at 36° Fahrenheit [2° Celsius].
Shipping quality: Good.
Resistance to insects: No unusual susceptibilities noted.
Resistance to diseases: No unusual susceptibilities noted.

Other Notes

Although the new variety of nectarine tree possesses the described characteristics under the ecological conditions at Le Grand, Calif., in the central part of the San Joaquin Valley, it is to be expected that variations in these characteristics may occur when farmed in areas with different climatic conditions, different soil types, and/or varying cultural practices.

I claim:

1. A new and distinct variety of nectarine tree, substantially as illustrated and described, that is most similar to its parent, 'Kay Sweet' (U.S. Plant Pat. No. 10,884) nectarine, by producing nectarines that are very firm in texture, clingstone in type, sub-acidic in flavor, yellow in flesh color, and full red in skin color, but is distinguished therefrom by producing fruit that is larger in size, that is sweeter in flavor, and that matures about eighteen days later.

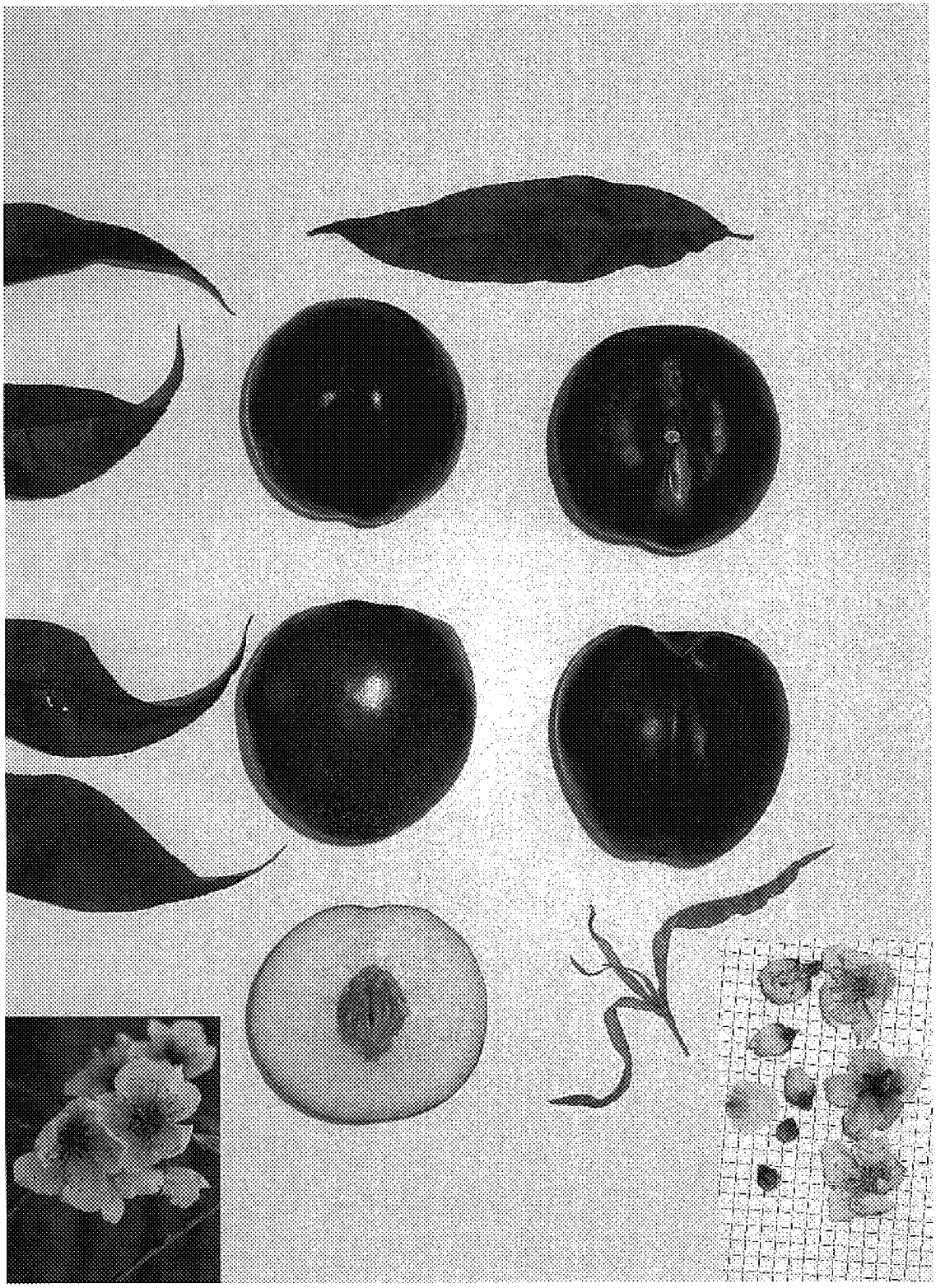

* * * * *